United States Patent
Yang et al.

(10) Patent No.: US 12,359,020 B2
(45) Date of Patent: Jul. 15, 2025

(54) CURABLE RESIN, CURABLE RESIN COMPOSITION, AND CURED PRODUCT

(71) Applicant: DIC Corporation, Tokyo (JP)

(72) Inventors: Lichen Yang, Chiba (JP); Ryuichi Matsuoka, Chiba (JP); Hiroyoshi Kannari, Chiba (JP)

(73) Assignee: DIC Corporation, Tokyo (JP)

( * ) Notice: Subject to any disclaimer, the term of this patent is extended or adjusted under 35 U.S.C. 154(b) by 532 days.

(21) Appl. No.: 17/917,232

(22) PCT Filed: Mar. 11, 2021

(86) PCT No.: PCT/JP2021/009703
§ 371 (c)(1),
(2) Date: Oct. 5, 2022

(87) PCT Pub. No.: WO2021/205806
PCT Pub. Date: Oct. 14, 2021

(65) Prior Publication Data
US 2023/0159695 A1    May 25, 2023

(30) Foreign Application Priority Data
Apr. 6, 2020   (JP) ................. 2020-068475

(51) Int. Cl.
| | | |
|---|---|---|
| C08G 61/02 | (2006.01) | |
| C07C 69/54 | (2006.01) | |
| C08F 12/34 | (2006.01) | |
| C08F 22/10 | (2006.01) | |
| C08G 61/12 | (2006.01) | |

(52) U.S. Cl.
CPC ............ *C08G 61/02* (2013.01); *C07C 69/54* (2013.01); *C08F 12/34* (2013.01); *C08F 22/1006* (2020.02); *C08G 61/127* (2013.01)

(58) Field of Classification Search
None
See application file for complete search history.

(56) References Cited

U.S. PATENT DOCUMENTS

| | | |
|---|---|---|
| 4,707,558 A | 11/1987 | Wang et al. |
| 4,786,700 A | 11/1988 | Zupancic et al. |
| 6,153,721 A * | 11/2000 | McCarthy ............... C07C 39/17 525/523 |
| 2024/0174790 A1* | 5/2024 | Pingitore ............... C08F 283/00 |

FOREIGN PATENT DOCUMENTS

| | | |
|---|---|---|
| JP | S6368537 | 3/1988 |
| JP | S6465110 | 3/1989 |
| JP | H101503238 | 11/1989 |
| JP | H0931006 | 2/1997 |
| JP | 2005314556 | 11/2005 |

OTHER PUBLICATIONS

"International Search Report (Form PCT/ISA/210) of PCT/JP2021/009703," mailed on Apr. 27, 2021, with English translation thereof, pp. 1-4.

* cited by examiner

*Primary Examiner* — David J Buttner
(74) *Attorney, Agent, or Firm* — JCIPRNET

(57) ABSTRACT

Provided is a cured product having excellent heat resistance and dielectric properties (low dielectric properties) by using a curable resin characterized by having an indane skeleton. Specifically, provided are a curable resin having an indane skeleton represented by the following formula, a resin composition containing the same, and a cured product thereof.

X is a (meth)acryloyl group; Ra and Rb are each an alkyl group, an aryl group, an aralkyl group, or a cycloalkyl group with a carbon atom number of 1 to 12; j is an integer of 1 to 3; k and l are each an integer of 0 to 4; n is an average number of repeating units, being 0.5 to 20; and m is an integer of 0 to 2.

6 Claims, 1 Drawing Sheet

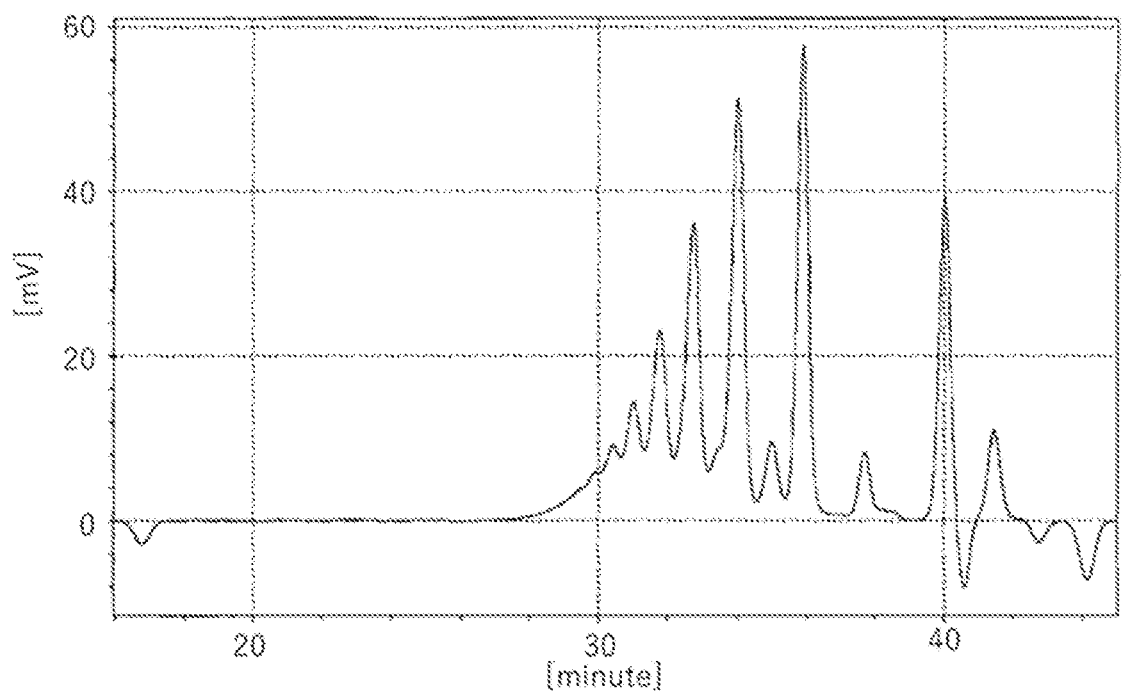

CURABLE RESIN, CURABLE RESIN COMPOSITION, AND CURED PRODUCT

CROSS-REFERENCE TO RELATED APPLICATION

This application is a 371 application of the International PCT application serial no. PCT/JP2021/009703, filed on Mar. 11, 2021, which claims the priority benefit of Japan Patent Application No. 2020-068475, filed on Apr. 6, 2020. The entirety of each of the above-mentioned patent applications is hereby incorporated by reference herein and made a part of this specification.

TECHNICAL FIELD

The present invention relates to a curable resin having an indane skeleton, a curable resin composition containing the curable resin, and a cured product obtained from the curable resin composition.

BACKGROUND ART

Along with an increase in the volume of information communication in recent years, information communication in high frequency bands has become to be performed vigorously, and electric insulating materials having more excellent electrical properties, in particular, a low dielectric constant and a low dielectric loss tangent have been demanded in order to reduce transmission loss in high frequency bands.

Furthermore, printed boards or electronic components in which these electric insulating materials are used are exposed to high-temperature solder reflow during mounting, and thus materials having excellent heat resistance and indicating a high glass transition temperature are required. Recently in particular, lead-free solders, which have high melting points, have been used from the viewpoint of environmental issues, and thus requirements for electric insulating materials with higher heat resistance have been increasing.

In response to these requirements, curable resins containing vinyl groups having various chemical structures have been conventionally developed. As such curable resins, curable resins such as divinylbenzyl ether of bisphenol and poly(vinylbenzyl) ether of novolac have been proposed, for example (refer to PTL 1 and PTL 2, for example). However, these vinylbenzyl ethers cannot give cured products with sufficiently small dielectric properties, and the obtained cured products are problematic for stable use in high frequency bands. Furthermore, divinylbenzyl ether of bisphenol does not have sufficiently high heat resistance.

For the vinylbenzyl ethers with improved properties, several poly(vinylbenzyl) ethers with specific structures have been developed in order to improve dielectric properties and the like (refer to PTL 3 to PTL 5, for example). However, although attempts to reduce the dielectric loss tangent and attempts to improve heat resistance have been made, improvement in these properties is still not sufficient, and further improvement in properties is desired.

Thus, conventional curable resins containing vinyl groups including poly(vinylbenzyl) ether do not provide cured products having both a low dielectric loss tangent required for electric insulating materials, especially for electric insulating materials ready for high frequency, and heat resistance capable of withstanding lead-free soldering.

CITATION LIST

Patent Literature

PTL 1: Japanese Unexamined Patent Application Publication No. S63-68537
PTL 2: Japanese Unexamined Patent Application Publication No. S64-65110
PTL 3: Japanese Translation of PCT Application Publication No. 1401-503238
PTL 4: Japanese Unexamined Patent Application Publication No. H09-31006
PTL 5: Japanese Unexamined Patent Application Publication No. 2005-314556

SUMMARY OF INVENTION

Technical Problem

Thus, an object of the present invention is to provide a cured product with excellent heat resistance and dielectric properties (low dielectric properties) by using a curable resin having an indane skeleton.

Solution to Problem

Thus, in order to achieve the object, the inventors of the present invention have earnestly studied to find out that a curable resin having an indane skeleton that can contribute to heat resistance and low dielectric properties and a cured product obtained from a curable resin composition containing the curable resin have excellent heat resistance and low dielectric properties to complete the present invention.

Specifically, the present invention relates to a curable resin having an indane skeleton represented by General Formula (1) below.

[Chemical Formula 1]

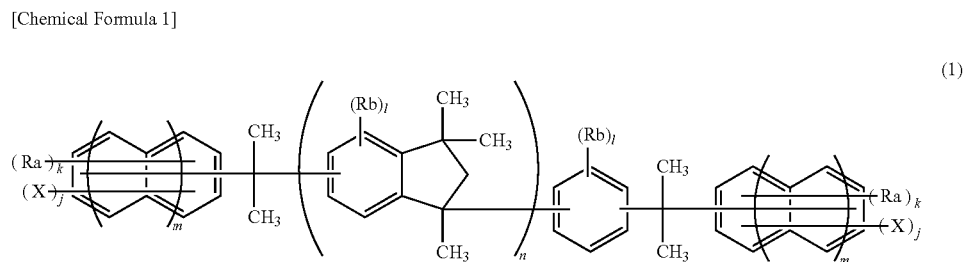

(1)

where in Formula (1) above, X represents a (meth) acryloyl group; Ra and Rb are each independently an alkyl group, an aryl group, an aralkyl group, or a cycloalkyl group with a carbon atom number of 1 to 12; j indicates an integer of 1 to 3; k and l each independently indicate an integer of 0 to 4; n is an average number of repeating units, indicating a value of 0.5 to 20; m indicates an integer of 0 to 2; and a straight line from Ra, X, and a carbon atom to an aromatic ring indicates that Ra, X, and a carbon atom may be bonded to any position on the aromatic ring.

The curable resin of the present invention is preferably a resin having an indane skeleton represented by General Formula (2) below:

[Chemical Formula 2]

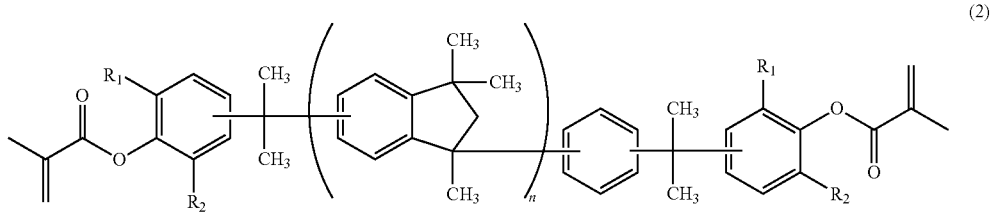

(2)

where in Formula (2) above, $R_1$ and $R_2$ are each independently a hydrogen atom or an alkyl group, an aryl group, an aralkyl group, or a cycloalkyl group with a carbon atom number of 1 to 12 and $R_1$ and $R_2$ are not both hydrogen atoms; and n is an average number of repeating units, indicating a value of 0.5 to 20.

The curable resin composition of the present invention preferably contains the curable resin.

The cured product of the present invention is preferably obtained by subjecting the curable resin composition to a curing reaction.

Advantageous Effects of Invention

The curable resin of the present invention can contribute to heat resistance and low dielectric properties, and thus a cured product obtained from a curable resin composition containing the curable resin has excellent heat resistance and dielectric properties (low dielectric properties) and is thus useful.

BRIEF DESCRIPTION OF DRAWING

FIG. 1 is a gel permeation chromatography (GPC) chart diagram of a curable resin having an indane skeleton obtained in Example 1.

DESCRIPTION OF EMBODIMENTS

The following describes the present invention in detail.
The present invention relates to a curable resin having an indane skeleton represented by General Formula (1) below:

[Chemical Formula 3]

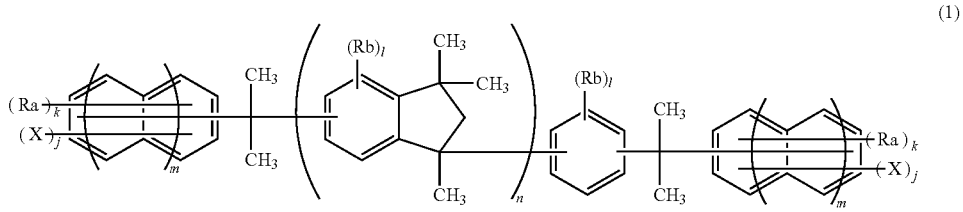

(1)

where in Formula (1) above, X represents a (meth) acryloyl group; Ra and Rb are each independently an alkyl group, an aryl group, an aralkyl group, or a cycloalkyl group with a carbon atom number of 1 to 12; j indicates an integer of 1 to 3; k and l each independently indicate an integer of 0 to 4; n is an average number of repeating units, indicating a value of 0.5 to 20; m indicates an integer of 0 to 2; and a straight line from Ra, X, and a carbon atom to an aromatic ring indicates that Ra, X, and a carbon atom may be bonded to any position on the aromatic ring.

The curable resin having an indane skeleton having an indane skeleton, which is low in polarity, reduces the proportion of polar functional groups in the structure of the curable resin and makes a cured product produced using the curable resin have excellent dielectric properties, which is preferred. The curable resin having an indane skeleton has excellent flexibility and pliability and also expects improvement in brittleness resistance, which is preferred.

In Formula (1) above, X is a (meth)acryloyl group to be a cross-linking group, that is, an acryloyl group or a methacryloyl group, which is particularly preferably a methacryloyl group. Having a (meth)acryloyl group in the curable resin provides a cured product having a lower dielectric loss tangent than that with other cross-linking groups (a vinyl benzyl ether group (a styryl group) and a dihydroxybenzene group, for example), which is a preferred mode.

Although the detailed reason why the cured product exhibiting low dielectric properties can be obtained by having the (meth)acryloyl group is not clear, in the case of a vinyl benzyl ether group (a styryl group) or the like contained in conventionally used curable resins, it has an ether group, which is a polar group, and in the case of having a dihydroxybenzene group, it has a plurality of hydroxy groups, which are polar groups, and it is presumed that the ester group based on the (meth)acryloyl group, as in the curable resin of the present invention, having lower molecular mobility contributes to those properties (having polar groups having high polarity such as an ether group and a hydroxy group tends to increase a dielectric constant and the dielectric loss tangent).

When the cross-linking group is a methacryloyl group, the structure contains a methyl group, and thus steric hindrance increases, and it is presumed that molecular mobility further reduces, resulting in a cured product with a much lower dielectric loss tangent, which is preferred. When there are a plurality of cross-linking groups, the cross-linking density increases, and heat resistance improves.

In Formula (1) above, Ra each independently represent an alkyl group, an aryl group, an aralkyl group, or a cycloalkyl group with a carbon atom number of 1 to 12 and preferably an alkyl group, an aryl group, or a cycloalkyl group with a carbon atom number of 1 to 4. Being an alkyl group with a carbon atom number of 1 to 12 or the like reduces the planarity in the vicinity of any of a benzene ring, a naphthalene ring, and an anthracene ring described below, and reduced crystallinity improves solvent solubility and lowers the melting point, which is a preferred mode. Having Ra provides steric hindrance, and it is presumed that molecular mobility further reduces, resulting in a cured product with a much lower dielectric loss tangent, which is preferred.

In Formula (1) above, Rb each independently represent an alkyl group, an aryl group, an aralkyl group, or a cycloalkyl group with a carbon atom number of 1 to 12 and preferably an alkyl group, an aryl group, or a cycloalkyl group with a carbon atom number of 1 to 4. Being an alkyl group with a carbon atom number of 1 to 12 or the like reduces the planarity in the vicinity of any of a benzene ring, a naphthalene ring, and an anthracene ring described below, and reduced crystallinity improves solvent solubility and lowers the melting point, which is a preferred mode.

In Formula (1) above, j indicates an integer of 1 to 3 and preferably an integer of 1 or 2. Being within the above range ensures flexibility, which is a preferred mode. By a plurality of X to be cross-linking groups being introduced to the same benzene ring or the like, the cross-linking groups hinder molecular mobility (inhibit each other), and even when Ra, which is a substituent, is not present, a cured product showing a low dielectric loss tangent can be obtained, which is preferred.

In Formula (1) above, k and l each independently indicate an integer of 0 to 4 and preferably an integer of 0 to 2. Being within the above range provides excellent reactivity, which is a preferred mode.

In Formula (1) above, m indicates an integer of 0 to 2, that is, m being 0 is a benzene ring, m being 1 is a naphthalene ring, and m being 2 is an anthracene ring; m being 0, or a benzene ring, is preferred. Being within the above range provides excellent solvent solubility, which is a preferred mode.

In Formula (1) above, n is an average number of repeating units and indicates a value of 0.5 to 20, which is preferably 0.5 to 5 and more preferably 0.95 to 2.5. Having the indane skeleton within the above range provides excellent solvent solubility, which is a preferred mode. If n is less than 0.5, the content proportion of a high melting point substance in the structure of the curable resin having an indane skeleton increases, resulting in poor solvent solubility, and furthermore, the proportion of a high molecular weight component contributing to flexibility is lowered, and thus the brittleness resistance of the obtained cured product reduces, and furthermore, the flexibility and the pliability may also reduce, which is not preferred. If n is larger than 20, the viscosity increases when dissolved in a solvent, furthermore, there is a concern that the heat resistance of the obtained cured product may be poor, and furthermore, the content of the high molecular weight component is extremely high, and there is a concern that when the cured product is molded, the fluidity may reduce, and the handleability may be poor, which is not preferred. The value of n is particularly preferably 0.95 to 2.5 from the viewpoints of the high heat deformation temperature, the high glass transition temperature, and the like of the cured product.

The curable resin having an indane skeleton introduces an alicyclic structure having an excellent balance between heat resistance and dielectric properties to the structure of the curable resin, and the cured product produced using the curable resin has an excellent balance between heat resistance and dielectric properties (especially a low dielectric loss tangent), and having a (meth)acryloyl group to be a cross-linking group in the molecular structure can exhibit much lower dielectric properties, which is preferred.

The curable resin of the present invention preferably has an indane skeleton represented by General Formula (2) below.

[Chemical Formula 4]

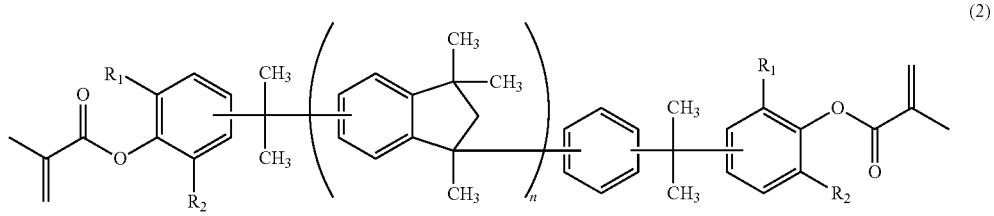

(2)

where in Formula (2) above, $R_1$ and $R_2$ are each independently a hydrogen atom or an alkyl group, an aryl group, an aralkyl group, or a cycloalkyl group with a carbon atom number of 1 to 12 and $R_1$ and $R_2$ are not both hydrogen atoms; and n is an average number of repeating units, indicating a value of 0.5 to 20.

In Formula (2) above, $R_1$ and $R_2$ are each independently a hydrogen atom or an alkyl group, an aryl group, an aralkyl group, or a cycloalkyl group with a carbon atom number of 1 to 12 and are not both hydrogen atoms and are each preferably an alkyl group, an aryl group, or a cycloalkyl group with a carbon atom number of 1 to 4. Being the alkyl group with a carbon atom number of 1 to 12 or the like reduces the planarity in the vicinity of the benzene ring, and reduced crystallinity improves solvent solubility and lowers the melting point, which is a preferred mode. Having $R_1$ and $R_2$ increases steric hindrance (only in the case of not being a hydrogen atom), and it is presumed that molecular mobility further reduces, resulting in a cured product with a much lower dielectric loss tangent, which is preferred.

In Formula (2) above, n is an average number of repeating units and indicates a value of 0.5 to 20, which is preferably 0.5 to 5 and more preferably 0.95 to 2.5. Having the indane skeleton within the above range provides excellent solvent solubility, which is a preferred mode. If n is less than 0.5, the content proportion of a high melting point substance in the structure of the curable resin having an indane skeleton increases, resulting in poor solvent solubility, and furthermore, the proportion of a high molecular weight component contributing to flexibility is lowered, and thus the brittleness resistance of the obtained cured product reduces, and furthermore, the flexibility and the pliability may also reduce, which is not preferred. If n is larger than 20, the viscosity increases when dissolved in a solvent, furthermore, there is a concern that the heat resistance of the obtained cured product may be poor, and furthermore, the content of the high molecular weight component is extremely high, and there is a concern that when the cured product is molded, the fluidity may reduce, and the handleability may be poor, which is not preferred. The value of n is particularly preferably 0.95 to 2.5 from the viewpoints of the high heat deformation temperature, the high glass transition temperature, and the like of the cured product.

The curable resin having an indane skeleton introduces an alicyclic structure having an excellent balance between heat resistance and dielectric properties to the structure of the curable resin, and the cured product produced using the curable resin has an excellent balance between heat resistance and dielectric properties (especially a low dielectric loss tangent), and having a methacryloyl group at the ends of the molecular structure provides a larger steric hindrance than that of an acryloyl group and can thus exhibit much lower dielectric properties, which is preferred.

<Method for Producing Intermediate Phenolic Compound>

As a method for producing the curable resins having an indane skeleton, the following first describes a method for producing an intermediate phenolic compound, which is a raw material (a precursor) for the curable resin having an indane skeleton.

General Formula (3) below is a compound in which Rc each independently indicate a monovalent functional group selected from the group consisting of General Formulae (4) and (5) below, the ortho position of at least one Rc of the two Rc is a hydrogen atom, and Rb and l indicate the same as above.

[Chemical Formula 5]

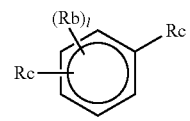

(3)

[Chemical Formula 6]

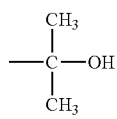

(4)

[Chemical Formula 7]

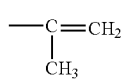

(5)

General Formula (6-1) below is a case in which m in General Formula (1) above is 0, that is, a case in which the curable resin having an indane skeleton is a benzene ring, in which i is preferably 1 or 2, and i is more preferably 1. General Formula (6-2) below is a case in which m in General Formula (1) above is 1, that is, a case in which the curable resin having an indane skeleton is a naphthalene ring, in which i is preferably 1 or 2, and i is more preferably 1. General Formula (6-3) below is a case in which m in General Formula (1) above is 2, that is, a case in which the curable resin having an indane skeleton is an anthracene ring, in which i is preferably 1 or 2, and i is more preferably 1. The curable resin having an indane skeleton having a hydroxy group (a phenolic hydroxy group) makes it possible to introduce a phenolic hydroxy group at the end in the structure, which is a preferred mode. Ra and k are each phenol or a derivative thereof, each of which indicates the same as above. By reacting the compound of General Formula (3) above with any compound of General Formulae (6-1) to (6-3) below in the presence of an acid catalyst, an intermediate phenolic compound indicated by General Formula (7) below can be obtained. Ra, Rb, k, l, i and n in General Formula (7) below indicate the same as above. General Formula (7) below exemplifies a case in which m in General Formula (1) above is 0, that is, a case of a benzene ring.

[Chemical Formula 8]

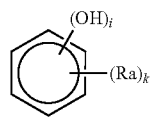

(6-1)

[Chemical Formula 9]

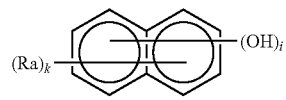

(6-2)

[Chemical Formula 10]

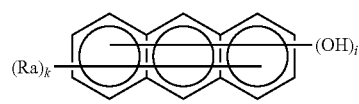

(6-3)

[Chemical Formula 11]

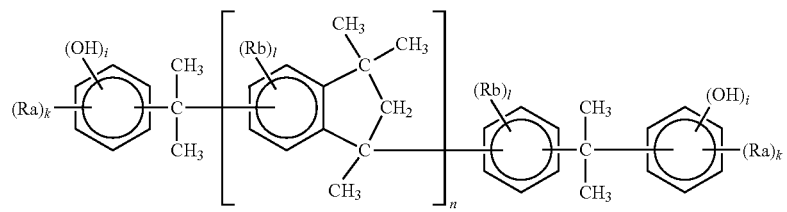

(7)

[Chemical Formula 12]

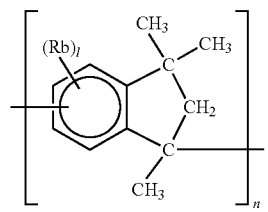

(8)

In the indane skeleton (refer to General Formula (8) above) as a characteristic of the intermediate phenolic compound, as to the average number n of repeating units, to provide a low melting point (a low softening point), a low melt viscosity, and excellent handleability, the average number n of repeating units indicates a value of 0.5 to 20, which is preferably 0.5 to 5 and more preferably 0.95 to 2.5. Having an indane skeleton in the structure of the intermediate phenolic compound provides excellent solvent solubility, which is a preferred mode. If n is less than 0.5, the content proportion of a high melting point substance in the structure of the intermediate phenolic compound increases, resulting in poor solvent solubility, and furthermore, the proportion of a high molecular weight component contributing to flexibility is lowered, and thus the brittleness resistance of the cured product obtained using the curable resin having an indane skeleton with the intermediate phenolic compound as the raw material (the precursor) reduces, and furthermore, the flexibility and the pliability may also reduce, which is not preferred. If n is larger than 20, the viscosity increases when dissolved in a solvent, there is a concern that the heat resistance of the obtained cured product may be poor, and furthermore, the content of the high molecular weight component is extremely high, and there is a concern that when the cured product is molded, the fluidity may reduce, and the handleability may be poor, which is not preferred.

The compound represented by General Formula (3) above for use in the present invention (hereinafter, a "compound (a)") is not limited to a particular compound. Typically used are p- and m-diisopropenylbenzene, p- and m-bis(α-hydroxyisopropyl)benzene (α,α'-dihydroxy-1,3-diisopropylbenzene), p- and m-bis(α-chloroisopropyl)benzene, 1-(α-hydroxyisopropyl)-3-isopropenylbenzene, 1-(α-hydroxyisopropyl)-4-isopropenylbenzene, or mixtures thereof. Nuclear alkyl substitution products of these compounds such as diisopropenyl toluene and bis(α-hydroxyisopropyl)toluene can also be used, and in addition, nuclear halogen substitution products of these compounds such as chlorodisopropenyl benzene and chlorobis(α-hydroxyisopropyl)benzene can also be used.

Other examples of the compound (a) include 2-chloro-1,4-diisopropenylbenzene, 2-chloro-1,4-bis(α-hydroxyisopropyl)benzene, 2-bromo-1,4-diisopropenylbenzene, 2-bromo-1,4-bis(α-hydroxyisopropyl)benzene, 2-bromo-1,3-diisopropenylbenzene, 2-bromo-1,3-bis(α-hydroxyisopropyl)benzene, 4-bromo-1,3-diisopropenylbenzene, 4-bromo-1,3-bis(α-hydroxyisopropyl)benzene, 5-bromo-1,3-diisopropenylbenzene, 5-bromo-1,3-bis(α-hydroxyisopropyl)benzene, 2-methoxy-1,4-diisopropenylbenzene, 2-methoxy-1,4-bis(α-hydroxyisopropyl)benzene, 5-ethoxy-1,3-diisopropenylbenzene, 5-ethoxy-1,3-bis(α-hydroxyisopropyl)benzene, 2-phenoxy-1,4-diisopropenylbenzene, 2-phenoxy-1,4-bis(α-hydroxyisopropyl)benzene, 2,4-diisopropenylbenzenethiol, 2,4-bis(α-hydroxyisopropyl)benzenethiol, 2,5-diisopropenylbenzenethiol, 2,5-bis(α-hydroxyisopropyl)benzenethiol, 2-methylthio-1,4-diisopropenylbenzene, 2-methylthio-1,4-bis(α-hydroxyisopropyl)benzene, 2-phenylthio-1,3-diisopropenylbenzene, 2-phenylthio-1,3-bis(α-hydroxyisopropyl)benzene, 2-phenyl-1,4-diisopropenylbenzene, 2-phenyl-1,4-bis(α-hydroxyisopropyl)benzene, 2-cyclopentyl-1,4-diisopropenylbenzene, 2-cyclopentyl-1,4-bis(α-hydroxyisopropyl)benzene, 5-naphthyl-1,3-diisopropenylbenzene, 5-naphthyl-1,3-bis(α-hydroxyisopropyl)benzene, 2-methyl-1,4-diisopropenylbenzene, 2-methyl-1,4-bis(α-hydroxyisopropyl)benzene, 5-butyl-1,3-diisopropenylbenzene, 5-butyl-1,3-bis(α-hydroxyisopropyl)benzene, 5-cyclohexyl-1,3-diisopropenylbenzene, and 5-cyclohexyl-1,3-bis(α-hydroxyisopropyl)benzene.

The substituent contained in the compound (a) is not limited to a particular substituent, and the above exemplified compounds can be used. In the case of substituents with large steric hindrance, compared to substituents with small steric hindrance, stacking of the obtained intermediate phenolic compound is less likely to occur, and crystallization of the intermediate phenolic compound is less likely to occur. In other words, the solvent solubility of the intermediate phenolic compound improves, which is a preferred mode.

The compound represented by any of General Formulae (6-1) to (6-3) above (hereinafter, a "compound (b)") is phenol or a derivative thereof and is not limited to a particular compound. Typical examples thereof include cresols such as o-cresol, m-cresol, and p-cresol; phenol; xylenols such as 2,3-xylenol, 2,4-xylenol, 2,5-xylenol, 2,6-xylenol (2,6-dimethylphenol), 3,4-xylenol, and 3,5-xylenol; ethylphenols such as o-ethylphenol, m-ethylphenol, and p-ethylphenol; butylphenols such as isopropylphenol, butylphenol, and p-t-butylphenol; alkylphenols such as p-pentylphenol, p-octylphenol, p-nonylphenol, and p-cumylphenol; halogenated phenols such as fluorophenol, chlorophenol, bromophenol, and iodophenol; monosubstituted phenols such as o-phenylphenol, p-phenylphenol, 2-cyclohexylphenol, 2-benzylphenol, aminophenol, nitrophenol, dinitrophenol, and trinitrophenol; fused polycyclic phenols such as 1-naphthol, 2-naphthol, 1-anthracenol, and 2-anthracenol; and polyvalent phenols such as resorcinol, alkylresorcinols, pyrogallol, catechol, alkylcatechols, hydroquinone, alkylhydroquinones, and phloroglucin.

These phenol and derivatives thereof may each be used alone, or two or more may be used in combination. Among them, the use of compounds in which two of the ortho positions and the para position with respect to the phenolic hydroxy group are alkyl substituted, such as 2,6-xylenol and 2,4-xylenol, is a more preferred mode, for example. However, if the steric hindrance is too large, there is a concern that it may hinder reactivity during synthesis of the intermediate phenolic compound, and thus it is preferable to use the compound (b) having an alkyl group with a carbon atom number of 1 to 4, for example.

In the method for producing the intermediate phenolic compound represented by General Formula (7) above for use in the present invention, the compound (a) and the compound (b) are prepared at a molar ratio of the compound (b) with respect to the compound (a) (the compound (b)/the compound (a)) of preferably 0.1 to 10 and more preferably 0.2 to 8 and are reacted in the presence of an acid catalyst, and thereby the intermediate phenolic compound having an indane skeleton can be obtained.

Examples of the acid catalyst for use in the reaction include inorganic acids such as phosphoric acid, hydrochloric acid, and sulfuric acid; organic acids such as oxalic acid, benzene sulfonic acid, toluene sulfonic acid, methanesulfonic acid, and fluoromethanesulfonic acid; solid acids such as activated white clay, acidic white clay, silica alumina, zeolite, and strongly acidic ion exchange resins; and heteropoly acid. Preferably used are oxalic acid, benzenesulfonic acid, toluene sulfonic acid, methanesulfonic acid, and fluoromethanesulfonic acid, which are homogeneous catalysts that can be easily removed after the reaction by neutralization with a base and washing with water.

As to the blending amount of the acid catalyst, the acid catalyst is blended in a range of 0.001 to 40 parts by mass with respect to 100 parts by mass of the total amount of the compound (a) and the compound (b) as the raw materials to be prepared first. From the viewpoints of handleability and economy, the amount is preferably 0.001 to 25 parts by mass.

The reaction temperature may be normally in a range of 50 to 300° C. and is preferably 80 to 200° C. in order to inhibit the formation of isomeric structures, avoid side reactions such as thermal decomposition, and obtain a highly pure intermediate phenolic compound.

The reaction time is usually in a range of a total of 0.5 to 24 hours and preferably in a range of a total of 0.5 to 12 hours under the reaction temperature condition because the reaction does not proceed completely in a short time, whereas side reactions such as a thermal decomposition reaction of the product occur in a long time.

In the method for producing the intermediate phenolic compound, although no other solvents are not necessarily required to be used because phenol or the derivative thereof also serves as a solvent, solvents can be used. In the case of a reaction system also serving as a dehydration reaction, for example, specifically, when reacted with a compound having an α-hydroxypropyl group as a raw material, a method of using an azeotropically dehydratable solvent such as toluene, xylene, or chlorobenzene to complete a dehydration reaction, then distilling off the solvent, and conducting the reaction in the range of the reaction temperature may be employed.

Examples of an organic solvent used for synthesizing the intermediate phenolic compound include ketones such as acetone, methyl ethyl ketone (MEK), methyl isobutyl ketone, cyclohexanone, and acetophenone; aprotic solvents such as N,N-dimethylformamide, N,N-dimethylacetamide, dimethyl sulfoxide, N-methyl-2-pyrrolidone, acetonitrile, and sulfolane; cyclic ethers such as dioxane and tetrahydrofuran; esters such as ethyl acetate and butyl acetate; aromatic solvents such as benzene, toluene, and xylene. These may be used alone or used by being mixed together.

The hydroxy group equivalent (the phenol equivalent) of the intermediate phenolic compound is preferably 200 to 2,000 g/eq and more preferably 220 to 500 g/eq from the viewpoint of heat resistance. The hydroxy group equivalent (the phenol equivalent) of the intermediate phenolic compound is calculated by the titration method, which refers to the neutralization titration method conforming to JIS K0070.
<Method for Producing Curable Resin Having Indane Skeleton>

The following describes a method for producing the curable resin having an indane skeleton (introduction of (meth)acryloyl groups).

The curable resin having an indane skeleton can be obtained by a known method such as the reaction of the intermediate phenolic compound with (meth)acrylic anhydride or (meth)acrylic acid chloride in the presence of a basic or acidic catalyst.

Examples of the (meth)acrylic anhydride include acrylic anhydride and methacrylic anhydride. Examples of the (meth)acrylic acid chloride include methacrylic acid chloride and acrylic acid chloride. These may each be used alone or used by being mixed together. Among them, methacrylic anhydride, which can produce a cured product with a much lower dielectric loss tangent, is preferably used.

Specific examples of the basic catalyst include dimethylaminopyridine, alkaline earth metal hydroxides, alkali metal carbonates, and alkali metal hydroxides. Specific examples of the acidic catalyst include sulfuric acid and methanesulfonic acid. Dimethylaminopyridine is particularly superior in terms of catalytic activity.

Examples of the reaction of the intermediate phenolic compound and the (meth)acrylic anhydride or the (meth)acrylic acid chloride (hereinafter may be referred to as "(meth)acrylic anhydride or the like") include a method of adding 1 to 5 moles of the (meth)acrylic anhydride or the like per mole of hydroxy groups contained in the intermediate phenolic compound and reacting them at a temperature of 30 to 150° C. for 1 to 40 hours while 0.03 to 1 of the basic catalyst is added in a batch or added gradually.

The reaction rate in the synthesis of the curable resin having an indane skeleton can be increased by using an organic solvent in combination during the reaction with the (meth)acrylic anhydride or the like (introduction of (meth)acryloyl groups). Such an organic solvent is not limited to a particular organic solvent. Examples thereof include ketones such as acetone and methyl ethyl ketone; alcohols such as methanol, ethanol, 1-propyl alcohol, isopropyl alcohol, 1-butanol, secondary butanol, and tertiary butanol, cellosolves such as methyl cellosolve and ethyl cellosolve; ethers such as tetrahydrofuran, 1,4-dioxane, 1,3-dioxane, and diethoxyethane; aprotic polar solvents such as acetonitrile, dimethyl sulfoxide, and dimethylformamide; and toluene. These organic solvents may each be used alone, or two or more may be used in combination as appropriate in order to adjust the polarity.

After the end of the reaction with the (meth)acrylic anhydride or the like (introduction of (meth)acryloyl groups) described above, the reaction product is washed with water, and then unreacted (meth)acrylic anhydride or the like and the organic solvent used together are distilled off under a heated and reduced pressure condition. Furthermore, to further reduce hydrolyzable halogens in the obtained curable resin having an indane skeleton, the curable resin having an indane skeleton can be dissolved again in an organic solvent such as toluene, methyl isobutyl ketone, or methyl ethyl ketone and further reacted with an aqueous solution of an alkali metal hydroxide such as sodium hydroxide or potassium hydroxide added. In this process, for the purpose of improving the reaction rate, a phase transfer catalyst such as a quaternary ammonium salt or a crown ether may be present. When the correlation transfer catalyst is used, the amount of the catalyst used is preferably in a range of 0.1 to 10% by mass with respect to the curable resin having an indane skeleton used. After the end of the reaction, the formed salt is removed by filtration or washing with water, the organic solvent is distilled off under a heated and reduced pressure condition, and thereby the objective curable resin having an indane skeleton with a low hydrolyzable chlorine content can be obtained.

The softening point of the curable resin having an indane skeleton is preferably 150° C. or lower and more preferably 30 to 100° C. When the softening point of the curable resin having an indane skeleton is within the above range, excellent processability is achieved, which is preferred.

<Curable Resin Composition>

The curable resin composition of the present invention preferably contains the curable resin having an indane skeleton. The curable resin having an indane skeleton having an indane skeleton provides excellent solvent solubility, makes it easy to prepare the curable resin composition, provides excellent handleability, and provides a low proportion of polar functional groups in the structure of the curable resin having an indane skeleton, and thus a cured product having excellent dielectric properties can be obtained.

[Other Resins and Others]

Alkenyl group-containing compounds such as bismaleimides, allyl ether-based compounds, allylamine-based compounds, triallyl cyanurate, alkenylphenol-based compounds, and vinyl group-containing polyolefin compounds can be added to the curable resin composition of the present invention, which can be used without any special limitations to the extent not impairing the purpose. Other thermosetting resins such as thermosetting polyimide resins, epoxy resins, phenolic resins, active ester resins, benzoxazine resins, and cyanate resins can also be blended as appropriate in accordance with the purpose.

[Curing Agent]

The curable resin composition of the present invention can contain curing agents. Examples of the curing agents include amine-based compounds, amide-based compounds, acid anhydride-based compounds, phenolic compounds, and cyanate ester compounds. These curing agents may be used alone, or two or more may be used in combination.

[Curing Accelerator]

The curable resin composition of the present invention can also contain curing accelerators in combination as appropriate as needed. Various types of curing accelerators can be used. Examples thereof include phosphorus compounds, tertiary amines, imidazoles, organic acid metal salts, Lewis acids, and amine complex salts. When used for semiconductor sealing materials in particular, phosphorus-based compounds such as triphenylphosphine or imidazoles are preferred due to their excellent curability, heat resistance, electric properties, moisture resistance reliability, and the like. These curing accelerators can be used alone, or two or more can be used in combination. The addition amount of the curing accelerator used is preferably in a range of 0.01 to 10 parts by mass with respect to 100 parts by mass of the epoxy resin, for example.

[Fire Retardant]

The curable resin composition of the present invention can be blended with non-halogenated fire retardants containing substantially no halogen atoms in order to exhibit fire retardancy as needed. Examples of the non-halogenated fire retardants include phosphorus-based fire retardants, nitrogen-based fire retardants, silicone-based fire retardants, inorganic fire retardants, and organometallic salt-based fire retardants, which can be used alone or in combination.

[Filler]

The curable resin composition of the present invention can be blended with inorganic fillers as needed. Examples of the inorganic fillers include fused silica, crystalline silica, alumina, silicon nitride, and aluminum hydroxide. When the blending amount of the inorganic fillers is made especially large, fused silica is preferably used. For the fused silica, although both crushed one and spherical one can be used, it is preferable to use mainly the spherical one in order to increase the blending amount of the fused silica and to control an increase in the melt viscosity of the molding material. To further increase the blending amount of the spherical silica, the particle size distribution of the spherical silica is preferably appropriately adjusted. When the curable resin composition is used for uses such as conductive pastes described below in detail, conductive fillers such as silver powder and copper powder can be used.

[Other Compounding Agents]

Various compounding agents such as silane coupling agents, mold release agents, pigments, and emulsifiers can be added to the curable resin composition of the present invention as needed.

<Cured Product>

The cured product of the present invention is preferably obtained by subjecting the curable resin composition to a curing reaction. The curable resin composition is obtained by the curable resin having an indane skeleton alone or uniformly mixing together the components such as the curing agents described above in addition to the curable resin having an indane skeleton and can be easily made into a cured product by the same method as conventionally known methods. Examples of the cured product include molded cured products such as laminates, cast products, adhesive layers, coatings, and films.

Examples of the curing reaction include heat curing and ultraviolet curing reactions. Among them, the heat curing reaction is easily carried out even under no catalyst, but when the reaction is desired to be conducted more quickly, the addition of polymerization initiators such as organic peroxides and azo compounds and basic catalysts such as phosphine-based compounds and tertiary amines is effective. Examples thereof include benzoyl peroxide, dicumyl peroxide, azobisisobutyronitrile, triphenylphosphine, triethylamine, and imidazoles.

<Uses>

The cured product obtained by the curable resin composition of the present invention has excellent heat resistance and dielectric properties and can thus suitably be used for heat-resistant members and electronic members. It can be particularly suitably used for prepregs, circuit boards, semiconductor sealing materials, semiconductor devices, build-up films, build-up boards, adhesives, and resist materials. It can also be suitably used for matrix resins of fiber-reinforced resins and is particularly suitable as prepregs with high heat resistance. In addition, the curable resin having an indane skeleton contained in the curable resin composition shows excellent solubility to various solvents and can thus be made into paints. The thus obtained heat-resistant members and electronic members can be suitably used for various uses including, but not limited to, industrial machine parts, general machine parts, parts for automobiles, railways, vehicles, and the like, space and aviation-related parts, electronic and electric parts, construction materials, container and packaging members, household goods, sports and leisure goods, and housing members for wind power generation.

EXAMPLES

The following describes the present invention specifically by means of examples and a comparative example. In the following, "part(s)" and "%" are on a mass basis unless otherwise specified. Curable resins and cured products obtained using the curable resins were synthesized under the following conditions, and furthermore, the obtained cured products were measured or calculated and evaluated under the following conditions.

<Gel Permeation Chromatography (GPC) Measurement (Evaluation of Number Average Molecular Weight and Average Number of Repeating Units)>

Measurement was conducted using the following measurement apparatus and measurement conditions to obtain GPC charts of the curable resins having an indane skeleton obtained by the method of synthesis indicated below. From the results of the GPC charts, the average number n of repeating units contributing to the indane skeleton in the curable resin having an indane skeleton was calculated based on the number average molecular weight (Mn) of the curable resin having an indane skeleton. Specifically, for compounds with n of 0 to 4, theoretical molecular weights and the respective actually measured molecular weights in GPC were plotted on a scatter diagram, an approximate straight line was drawn, the number average molecular weight (Mn) was determined from a point indicated by an actually measured value Mn(1) on the straight line, and the average number n of repeating units was calculated.

Measurement apparatus: "HLC-8320 GPC" manufactured by Tosoh Corporation

Column: Guard column "HXL-L" manufactured by Tosoh Corporation+"TSK-GEL G2000HXL" manufactured by Tosoh Corporation+"TSK-GEL G2000HXL" manufactured by Tosoh Corporation "TSK-GEL G3000HXL" manufactured by Tosoh Corporation+"TSK-GEL G4000HXL" manufactured by Tosoh Corporation Detector: RI (differential refractometer)

Data processing: "GPC Workstation EcoSEC-WorkStation" manufactured by Tosoh Corporation Measurement conditions: Column temperature 40° C.

Developing solvent tetrahydrofuran

Flow rate 1.0 ml/minute

Standard: The following monodispersed polystyrenes of known molecular weights were used in conformity with the measurement manual of the "GPC Workstation EcoSEC-WorkStation."

(Polystyrenes Used)
 "A-500" manufactured by Tosoh Corporation
 "A-1000" manufactured by Tosoh Corporation
 "A-2500" manufactured by Tosoh Corporation
 "A-5000" manufactured by Tosoh Corporation
 "F-1" manufactured by Tosoh Corporation
 "F-2" manufactured by Tosoh Corporation
 "F-4" manufactured by Tosoh Corporation
 "F-10" manufactured by Tosoh Corporation
 "F-20" manufactured by Tosoh Corporation
 "F-40" manufactured by Tosoh Corporation
 "F-80" manufactured by Tosoh Corporation
 "F-128" manufactured by Tosoh Corporation Sample: A microfiltered tetrahydrofuran solution (50 μl) of 1.0% by mass in terms of solid content of the curable resin having an indane skeleton obtained in the synthetic example.

Example 1

To a 1 L flask equipped with a thermometer, a cooling tube, a Dean-Stark trap, and a stirrer, 48.9 g (0.4 mol) of 2,6-dimethylphenol, 272.0 g (1.4 mol) of α,α'-dihydroxy-1,3-diisopropylbenzene, 280 g of xylene, and 70 g of activated white clay were charged and were heated up to 120° C. with stirring. Furthermore, the temperature was increased up to 210° C. while the distilled water was removed with a Dean-Stark tube, and the reaction was conducted for 3 hours. Subsequently, the product was cooled to 140° C., 146.6 g (1.2 mol) of 2,6-dimethylphenol was charged thereto, then the temperature was increased up to 220° C., and they were reacted for 3 hours. After the reaction, the product was air-cooled to 100° C. and was diluted with 300 g toluene, the activated white clay was filtered out, and the solvent and low molecular weight substances such as unreacted substances were distilled off to obtain 365.3 g of an intermediate phenolic compound. The hydroxy group equivalent (the phenol equivalent) of the obtained intermediate phenolic compound was 299.

To a 2 L flask equipped with a thermometer, a cooling tube, and a stirrer, 365.3 g of the obtained intermediate phenolic compound and 700 g of toluene were charged and were stirred at about 85° C. Next, 29.9 g (0.24 mol) of dimethylaminopyridine was charged thereto, and when all the solids appeared to be dissolved, 277.5 g (1.8 mol) of methacrylic anhydride was added dropwise thereto over 1 hour. After the dropwise addition ended, the reaction was further conducted at 85° C. for 3 hours. The reaction solution was added dropwise to 4,000 g of methanol, which was stirred vigorously with a magnetic stirrer in a 5 L beaker, over 1 hour. The obtained precipitate was filtered under reduced pressure through a membrane filter and was dried to obtain a curable resin having an indane skeleton of the following structural formula (the average number n of repeating units=1.6). The average number n of repeating units was calculated by performing GPC measurement, the GPC chart of which is FIGURE, and using the number average molecular weight (Mn). In the following, the average number n of repeating units was calculated in the same manner for the other examples and the comparative example.

[Chemical Formula 13]

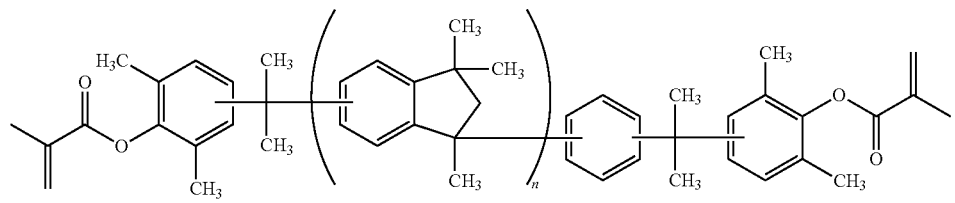

Example 2

Synthesis was carried out by the same method as in Example 1 above except that methacrylic anhydride in Example 1 above was changed to 227.0 g (1.8 mol) of acrylic anhydride to obtain a curable resin having an indane skeleton of the following structural formula (the average number n of repeating units=1.6).

[Chemical Formula 14]

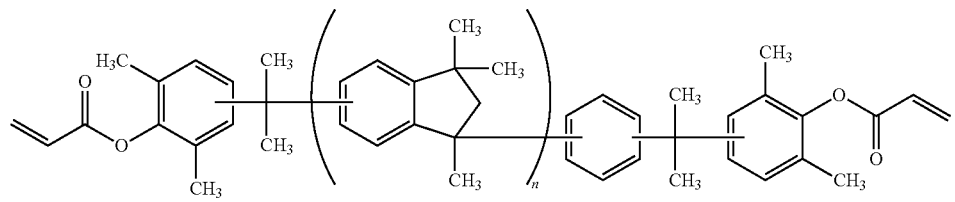

Example 3

Synthesis was carried out by the same method as in Example 1 above except that 2,6-dimethylphenol in Example 1 above was changed to 306.3 g (1.8 mol) of o-phenylphenol to obtain a curable resin having an indane skeleton of the following structural formula (the average number n of repeating units=1.6).

[Chemical Formula 15]

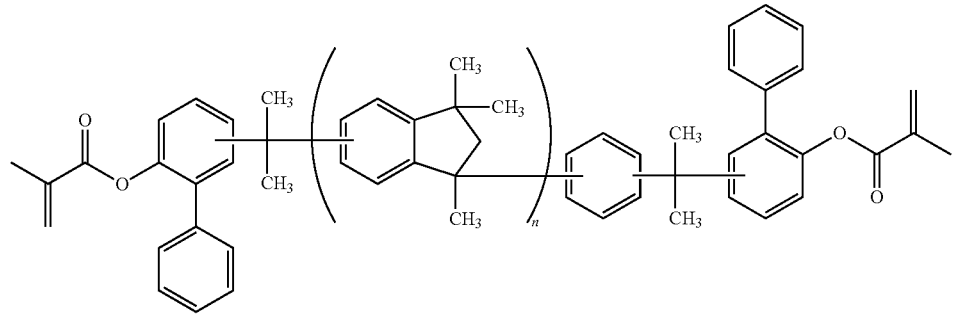

Example 4

Synthesis was carried out by the same method as in Example 1 above except that 2,6-dimethylphenol in Example 1 above was changed to 317.3 g (1.8 mol) of 2-cyclohexylphenol to obtain a curable resin having an indane skeleton of the following structural formula (the average number n of repeating units=1.6).

[Chemical Formula 16]

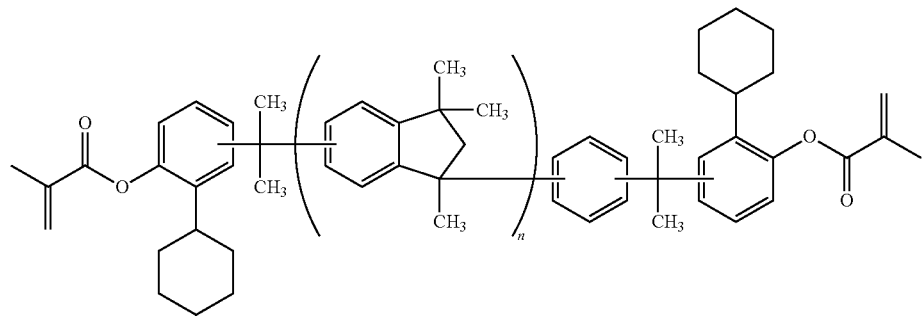

Example 5

Synthesis was carried out by the same method as in Example 1 above except that 2,6-dimethylphenol in Example 1 above was changed to 331.6 g (1.8 mol) of 2-benzylphenol to obtain a curable resin having an indane skeleton of the following structural formula (the average number n of repeating units=1.6).

[Chemical Formula 17]

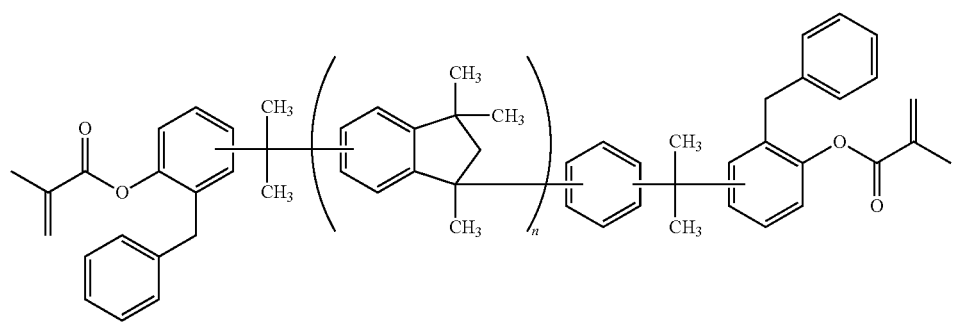

Example 6

Synthesis was carried out by the same method as in Example 1 above except that 2,6-dimethylphenol in Example 1 above was changed to 169.4 g (1.8 mol) of phenol to obtain a curable resin having an indane skeleton of the following structural formula (the average number n of repeating units=1.6).

[Chemical Formula 18]

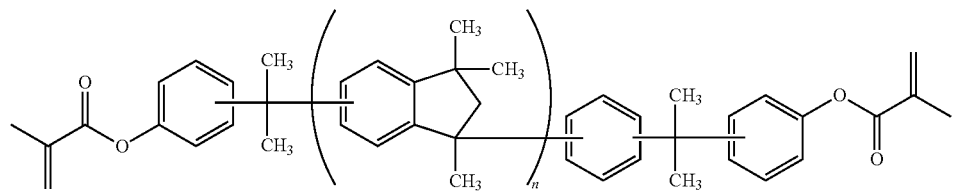

Example 7

Synthesis was carried out by the same method as in Example 1 above except that 2,6-dimethylphenol in Example 1 above was changed to 198.2 g (1.8 mol) of catechol and the addition amount of methacrylic anhydride was changed to 555.0 g (1.8×2 mol) to obtain a curable resin having an indane skeleton of the following structural formula (the average number n of repeating units=1.6).

[Chemical Formula 19]

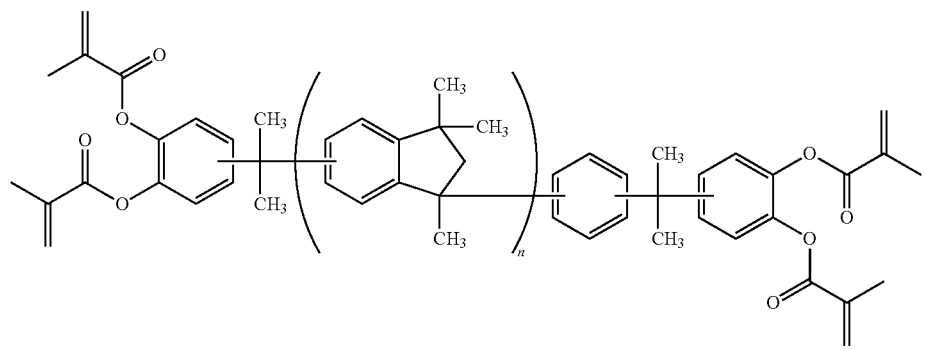

Example 8

Synthesis was carried out by the same method as in Example 1 above except that 2,6-dimethylphenol in Example 1 above was changed to 227.0 g (1.8 mol) of pyrogallol and the addition amount of methacrylic anhydride was changed to 832.5 g (1.8×3 mol) to obtain a curable resin having an indane skeleton of the following structural formula (the average number n of repeating units=1.6).

[Chemical Formula 20]

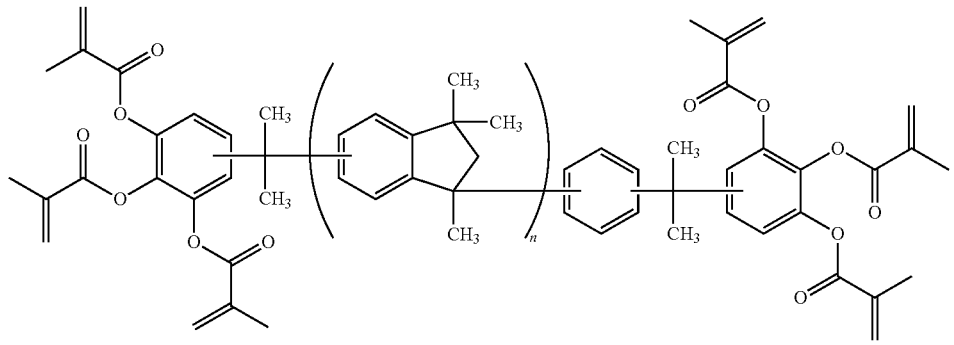

Example 9

Synthesis was carried out by the same method as in Example 1 above except that 2,6-dimethylphenol in Example 1 above was changed to 259.5 g (1.8 mol) of 2-naphthol to obtain a curable resin having an indane skeleton of the following structural formula (the average number n of repeating units=1.6).

[Chemical Formula 21]

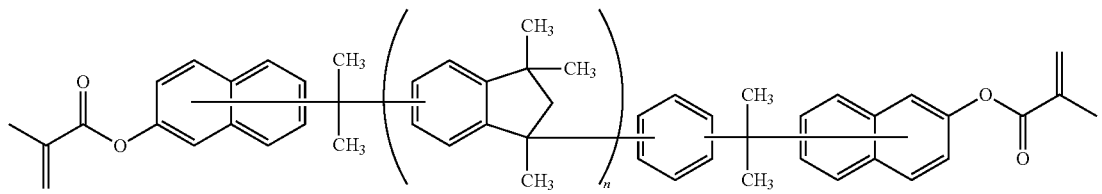

Comparative Example 1

To a 1 L flask equipped with a thermometer, a cooling tube, a Dean-Stark trap, and a stirrer, 48.9 g (0.4 mol) of 2,6-dimethylphenol, 272.0 g (1.4 mol) of α,α'-dihydroxy-1,3-diisopropylbenzene, 280 g of xylene, and 70 g of activated white clay were charged and were heated up to 120° C. with stirring. Furthermore, the temperature was increased up to 210° C. while the distilled water was removed with a Dean-Stark tube, and the reaction was conducted for 3 hours. Subsequently, the product was cooled to 140° C., 146.6 g (1.2 mol) of 2,6-dimethylphenol was charged thereto, then the temperature was increased up to 220° C., and they were reacted for 3 hours. After the reaction, the product was air-cooled to 100° C. and was diluted with 300 g toluene, the activated white clay was filtered out, and the solvent and low molecular weight substances such as unreacted substances were distilled off to obtain 365.3 g of an intermediate phenolic compound. The hydroxy group equivalent (the phenol equivalent) of the obtained intermediate phenolic compound was 299.

To a 2 L flask equipped with a thermometer, a cooling tube, and a stirrer, 365.3 g of the obtained intermediate phenolic compound, 0.184 g (0.001 mol) of 2,4-dinitrophenol (2,4-DNP), 23.5 g (0.073 mol) of tetrabutylammonium bromide (TBAB), 209 g (1.37 mol) of chloromethylstyrene, and 400 g of methyl ethyl ketone were added, and the temperature was increased up to 75° C. with stirring. Then, 48%-NaOHaq was added dropwise to the reaction vessel kept at 75° C. over 20 minutes. After the dropwise addition ended, stirring was further continued at 75° C. for 4 hours. After 4 hours, the product was cooled to room temperature, 100 g of toluene was added thereto, and furthermore, 10% HCl was added thereto to be neutralized. Subsequently, the aqueous phase was separated, and furthermore, separation washing was performed three times with 300 mL of water. The obtained organic phase was concentrated by distillation, and methanol was added to reprecipitate the product. The precipitate was filtered out and dried to obtain a curable resin having an indane skeleton of the following structural formula (the average number n of repeating units=1.6).

[Chemical Formula 22]

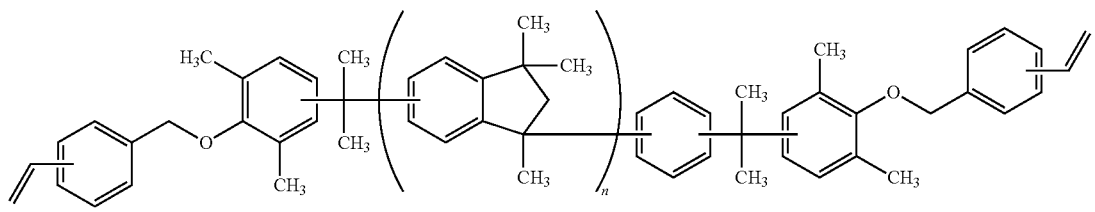

<Production of Resin Film (Cured Product)>

Each of the curable resins (solid powders) obtained in the examples and the comparative example was put into a square mold frame 5 cm square, was held between stainless plates, and was set in a vacuum press. It was pressurized up to 1.5 MPa under normal pressure and temperature. Next, the pressure was reduced to 10 torr and was then heated up to a temperature 50° C. above a thermosetting temperature over 30 minutes. Furthermore, the product was left at rest for 2 hours and was then slowly cooled to room temperature. Thus, a uniform resin film (a cured product) with an average film thickness of 100 μm was produced.

<Evaluation of Heat Resistance>

For the obtained resin film (cured product), using a DSC apparatus (Pyris Diamond) manufactured by Perkin Elmer, a peak exothermic temperature (a thermosetting temperature) observed when measured at a temperature increase condition of 20° C./minute from room temperature was observed, and then it was held at a temperature 50° C. above it for 30 minutes. Next, the sample was cooled to room temperature at a temperature decrease condition of 20° C./minute, and furthermore, the temperature was again increased at a temperature increase condition of 20° C./minute to measure the glass transition temperature (Tg) (° C.) of the resin film (the cured product). As to the glass transition temperature (Tg), if it is 100° C. or higher, there is no problem in practical use, and it is preferably 150° C. or higher.

<Evaluation of Dielectric Properties>

As to the dielectric properties of the obtained resin film (cured product) in the in-plane direction, a dielectric constant and a dielectric loss tangent were measured at a frequency of 10 GHz by the split-post dielectric resonator method using a network analyzer N5247A of Keysight Technologies. As to the dielectric loss tangent, if it is $10 \times 10^{-3}$ or less, there is no problem in practical use, and it is preferably $7.5 \times 10^{-3}$ or less; as to the dielectric constant, if it is 3 or less, there is no problem in practical use, and it is preferably 2.7 or less and more preferably 2.5 or less.

From the evaluation results in Table 1 above, it was confirmed that in Examples 1 to 9 the cured products obtained by using the curable resins had excellent heat resistance and dielectric properties (especially a low dielectric loss tangent). Among them, in Examples 1 and 3 to 6, in which the curable resins having one methacryloyl group at each end in the structure of the curable resins were used, a reduction in the dielectric constant was observed and improvement in low dielectric properties was observed. In Examples 7 and 8, which have a plurality of methacryloyl groups at each end in the structure of the curable resins, improvement in heat resistance was observed. On the other hand, in Comparative Example 1, there is no (meth)acryloyl group in the curable resin having an indane skeleton, and thus it was confirmed that the dielectric loss tangent was higher than those of the examples, thus failing to achieve both heat resistance and dielectric properties.

INDUSTRIAL APPLICABILITY

The cured product obtained by using the curable resins of the present invention has excellent heat resistance and dielectric properties and can thus suitably be used for heat-resistant members and electronic members. It can be particularly suitably used for prepregs, semiconductor sealing materials, circuit boards, build-up films, build-up boards, adhesives, and resist materials. It can also be suitably used for matrix resins of fiber-reinforced resins and is suitable as prepregs with high heat resistance.

TABLE 1

| Value of physical properties | Example 1 | Example 2 | Example 3 | Example 4 | Example 5 | Example 6 | Example 7 | Example 8 | Example 9 | Comparative Example 1 |
|---|---|---|---|---|---|---|---|---|---|---|
| Dielectric loss tangent ($\times 10^{-3}$) | 2.0 | 7.1 | 1.8 | 1.9 | 1.7 | 4.0 | 2.2 | 2.1 | 3.2 | 8.2 |
| Dielectric constant | 2.5 | 2.7 | 2.4 | 2.2 | 2.3 | 2.5 | 2.7 | 2.7 | 2.3 | 2.7 |
| Tg (° C.) | 153 | 106 | 173 | 164 | 162 | 150 | 189 | 190 | 165 | 120 |

What is claimed is:

1. A curable resin comprising an indane skeleton represented by General Formula (1) below:

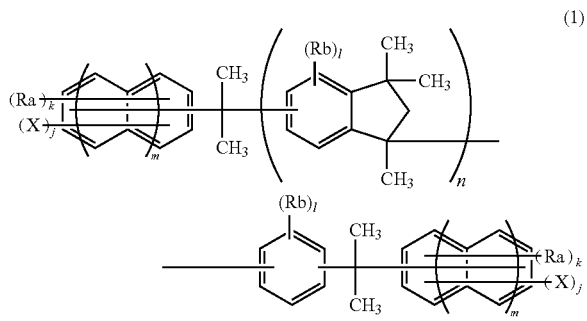

where in Formula (1) above, X represents a (meth)acryloyl group; Ra and Rb are each independently an alkyl group, an aryl group, an aralkyl group, or a cycloalkyl group with a carbon atom number of 1 to 12; j indicates an integer of 1 to 3; k and l each independently indicate an integer of 0 to 4; n is an average number of repeating units, indicating a value of 0.5 to 20; m indicates an integer of 0 to 2; and a straight line from Ra, X, and a carbon atom to an aromatic ring indicates that Ra, X, and a carbon atom may be bonded to any position on the aromatic ring.

2. The curable resin according to claim 1 comprising an indane skeleton represented by General Formula (2) below:

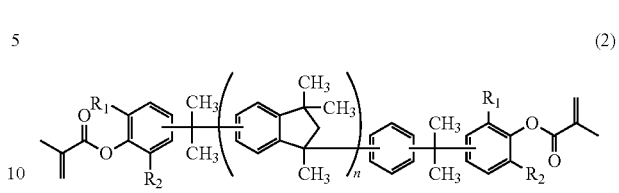

where in Formula (2) above, $R_1$ and $R_2$ are each independently a hydrogen atom or an alkyl group, an aryl group, an aralkyl group, or a cycloalkyl group with a carbon atom number of 1 to 12 and $R_1$ and $R_2$ are not both hydrogen atoms; and n is an average number of repeating units, indicating a value of 0.5 to 20.

3. A curable resin composition comprising the curable resin according to claim 1.

4. A cured product obtained by subjecting the curable resin composition according to claim 3 to a curing reaction.

5. A curable resin composition comprising the curable resin according to claim 2.

6. A cured product obtained by subjecting the curable resin composition according to claim 5 to a curing reaction.

* * * * *